United States Patent [19]

Lipton

[11] Patent Number: 5,504,012
[45] Date of Patent: Apr. 2, 1996

[54] METHOD FOR FIXING FECAL SAMPLES

[76] Inventor: Stewart Lipton, 708 Clearview Dr., Glenview, Ill. 60025

[21] Appl. No.: 414,616

[22] Filed: Mar. 31, 1995

Related U.S. Application Data

[62] Division of Ser. No. 165,042, Dec. 10, 1993, Pat. No. 5,453,381.

[51] Int. Cl.$^6$ ....................................................... G01N 1/28
[52] U.S. Cl. ................................................. 436/176; 436/17
[58] Field of Search ................................... 436/8, 17–18, 436/174, 176; 424/3

Primary Examiner—Lyle A. Alexander
Attorney, Agent, or Firm—Fitch, Even, Tabin & Flannery

[57] ABSTRACT

This invention provides methods and compositions for the analysis of parasites in fecal samples. A parasitological fixative is provided which contains glyceraldehyde, a salt of an organic acid, organic solvent and water. The parasitological fixative does not contain formaldehyde, formalin or other harmful chemicals commonly associated with fixative compositions. The invention further describes a slide fixative composition comprising a protein solution, glycerin and an adhesion enhancing agent which improves the adhesion of sample components to a microscope slide.

16 Claims, No Drawings

METHOD FOR FIXING FECAL SAMPLES

This is a division of application Ser. No. 08/165,042, filed Dec. 10, 1993 now U.S. Pat. No. 5,453,381.

This invention relates to a method for fixing and analyzing fecal samples for the detection and identification of parasites. More specifically, the invention provides a method for fixing fecal samples in a parasitological fixative composition which is free of formaldehyde, formalin, mercury, phenol and other harmful chemicals commonly associated with fixatives, and a slide fixative composition which improves the adhesion of sample components to a microscope slide.

BACKGROUND OF THE INVENTION

Diagnosis of intestinal parasitic disease is confirmed by recovery and identification of helminth eggs and larvae or protozoan trophozoites and/or cysts in fecal samples. One of the problems faced by the parasitologist is the delay between collection and examination of specimens. Since trophozoites deteriorate quickly outside of the host, it has been difficult in the past to deliver or ship fecal samples to offsite laboratories for accurate diagnosis or to hold the sample for diagnosis at a later time. Even though organisms are present in specimens when first obtained from the patient, they may be unrecognizable or completely disintegrated by the time they are processed, leading to inaccurate diagnosis.

Investigators have emphasized the importance of proper collection of samples for the diagnosis of infections by helminths, especially protozoa. Unless samples are examined immediately after defecation, or are preserved in a suitable fixative, many infections may be missed due to the short lives of the protozoan trophozoites (Yang et al. 67 Amer. J. Clin. Pathol. 300 (1977)).

To overcome the problems associated with the examination of fecal samples, a number of fixatives have been proposed for the preservation of trophozoites and other diagnostic stages in recognizable form. These include fixatives whose composition comprises compounds such as formaldehyde, formalin, mercury, phenol, and polyvinyl alcohol (PVA). However, the use of these types of preservatives results in a number of disadvantages.

The use of formaldehyde, mercury and phenol containing preservatives raises environmental and health concerns. Vapors of formaldehyde and phenol are intensely irritating to mucous membranes, and topical application may produce acute dermatitis. Further, mercury compounds are readily absorbed via the respiratory tract, intact skin and gastrointestinal tract, and can contribute to physiological problems including neurological disorders. Mercury has also been known to bioaccumulate in the environment, resulting in environmental problems.

In addition to the health and environmental problems associated with formaldehyde and mercury based preservatives, the use of these type of preservatives limits the procedures used to analyze the preserved sample. A commonly used diagnostic method utilizes a two-vial kit for collecting stool specimens (Brooke, 4 Triangle 326 (1960)). In accordance with the two-vial method, the person collecting the specimen is directed to introduce portions of the specimen into a vial containing a formalin solution, and into a second vial containing PVA fixative. Hence, the two-vial method requires the collection of two separate fecal samples in order to provide a complete analysis.

Subsequent processing of specimens taken using the two-vial method result in undesirable process steps. For example, the formalin fixed sample is concentrated with filtration, centrifugation and partitioning with an organic solvent, such as ether or ethyl acetate. The sample is utilized for the detection of cysts, eggs and larvae. The second specimen, which was fixed in PVA, is spread on a microscope slide, stained and examined for cysts and trophozoites. Hence, the processing of formaldehyde or formalin fixed specimens requires concentration steps which utilize organic solvents and which can result in the loss of parasites from the sample (see Examples).

The use of formaldehyde or formalin as a fixative also results in limitations on the types of staining and detection techniques that can be subsequently utilized. For example, the use of specific antibodies to detect particular cell types is commonly used in histological applications. Antibodies can recognize and bind to specific receptors on a cell. The bound antibody is rendered detectable through techniques which include fluorescent or radioactive labels. The chemical action of formaldehyde tends to alter receptive sites on cells and thus render them undetectable with antibody. Hence, the use of a formaldehyde based fixative precludes the use of potentially useful immunoassay methods.

Attempts have been made to alleviate some of the problems associated with previous methods for fixing and analyzing fecal samples for parasites. For example, the Para-Pak™ product (sold by Meridian Diagnostics, Inc. Cincinnati, Ohio) provides a multipurpose fixative-preservative which allows for the recovery and identification of all stages of intestinal parasites. However, the fixative contains formaldehyde which results in all of the aforementioned disadvantages.

Formaldehyde substitutes have also been described. For example, U.S. Pat. No. 3,546,334 to Lerner et al. describes a cytological fixative and protective composition that includes a liquid solution of alcohol, water, polyethylene glycol, acetone and optionally a dye. The composition is applied directly to a smear of cells on a microscope slide to provide a method for simultaneously fixing the specimen on the slide and protecting it with a coating. The '334 patent does not suggest that its composition could be useful for fixing fecal specimens and makes no suggestion that its claimed composition would be useful for fixing and subsequent examination of samples containing parasites.

Formalin replacements which are diagnostically equivalent to formaldehyde but are 100% free of formaldehyde and glutaraldehyde also available (sold as NoToX™ Histological Fixative, Earth Safe Industries, Inc. Belle Mead, N.J.). The formalin substitute is described as a unique bis carbonyl compound and as being useful for the preservation of histological samples. Its use for the preservation of fecal samples is not described or suggested. Further, the NoToX™ formalin replacement had an unacceptably high pH, did not provide clear nuclear definition of cysts, and was found to be unacceptable for the fixation and subsequent analysis of fecal samples for parasites.

In addition to the problems associated with formaldehyde preservatives, conventional techniques for applying fixed sample material to a microscope slide and subsequent staining procedures often can result in loss of sample from the slide. In accordance with commonly accepted practice, specimens which have been fixed in PVA, and formalin fixed samples which have been concentrated are applied as a smear to a microscope slide. In some methods, albumin is mixed with the specimen prior to its application to the slide (Technical Literature for Para-Pak™ Fixative, Meridian Diagnostics, Inc. Cincinnati, Ohio). Smears are usually allowed to air dry and are then stained through a process which includes subjecting the smear to a series of staining and washing steps with organic solvents and aqueous solutions. During the staining and washing steps, sample can be lost from the slide, resulting in the need for repeat analysis or inaccurate diagnosis.

An object of this invention is to provide a fixative composition which does not contain formaldehyde, formalin, mercury or other harmful chemicals commonly associated with fixative compositions.

Another objective of this invention is to provide a method of using the fixative composition in a process for fixing, concentrating and staining fecal specimens being analyzed for ova or parasites such that only one fecal specimen is needed for both concentrating and staining fecal specimens being analyzed for ova or parasites.

Another important objective of this invention is to provide a method which does not require an organic solvent extraction step and does not result in the loss of parasites during concentration of the sample.

Another objective of this invention is to provide a method of fixing fecal samples which does not preclude the use of immunoassay techniques.

Yet another objective of this invention is to provide method that utilizes a slide fixative composition that results in improved adhesion of sample to a microscope slide.

Further objects and advantages of the invention will be found by reference to the following description.

SUMMARY OF THE INVENTION

The invention provides a method for fixing, concentrating and staining fecal specimens being analyzed for ova and parasites. The method of the invention comprises the use of a parasitological fixative which contains no formaldehyde, formalin, phenol, mercury or other harmful chemicals. In accordance with the method of the invention, the collection of only one fecal sample is required. The method does not require the use of organic solvents during sample processing, which results in increased recoveries of parasites. Fecal samples processed according to the method of the invention can be stained by commonly available methods, including immunoassay techniques.

In an important aspect of the invention, the parasitological fixative comprises from about 3 to about 5 weight percent glyceraldehyde, from about 1 to about 2 weight percent of the salt of an organic acid of up to about 6 carbon atoms, organic solvent and water. A single fecal sample preserved in the parasitological fixative of the invention can be utilized for the detection of all diagnostic stages, including cysts, eggs, larvae and protozoa trophozoites, hence eliminating the need for two separate fecal samples.

In another important aspect, the method of the invention further provides for the use of a slide fixative which results in the improved adhesion of sample material to the microscope slide. The slide fixative comprising from about 40 weight % to about 60 weight % of a protein solution; from about 40 weight % to about 60 weight % glycerin and from about 0.1 to about 0.9 weight percent of an adhesion enhancing agent.

The method of the invention comprises contacting a fecal specimen with an effective amount of a parasitological fixative, said fixative comprising from about 40 to about 60 weight percent glyceraldehyde, from about 1 to about 2 weight percent of the salt of an organic acid of up to about 6 carbon atoms, organic solvent and water. The fixed fecal specimen is then concentrated through a method comprising filtration and centrifugation. About one drop of the sedimented fecal sample is mixed on a microscope slide such that parasites in the fecal specimen are rendered detectable by microscopic examination. The remaining sedimented fecal sample is mixed with a slide fixative, said slide fixative comprising from about 40 to about 60 weight percent of a protein solution; from about 40 to about 60 weight percent glycerin and from about 0.1 to about 0.9 weight percent of an adhesion enhancing agent. About one drop of the sample/slide fixative mixture is applied to a microscope slide and stained for the identification of parasites. Fecal samples processed according to the method of the invention can be stained by a number of staining techniques, including trichrome staining, modified trichrome staining, modified acid fast staining, hematoxylin stain, fluorescent stains, and the use of immunoassay staining techniques.

DETAILED DESCRIPTION OF THE INVENTION

As used herein the term "parasite" includes protozoa, helminths and all intestinal worms. The term "protozoa" describes a major division of protists, a heterogeneous group in which there are well over 30,000 species. Protozoa are microscopic animals, each consisting of a single cell or groups of cells to form a colony. The protozoa are classified into five major groups based on differences in their mechanism of locomotion. The five major groups include: Sarcodina (amebae), which move by protoplasmic flow with the formation of pseudopodia; Ciliata (ciliates), which move by cilia; Suctoria (suctorians), where young stages are ciliated and adult stages are sessile and provided with tentacles; Mastigophora (flagellates), which move by flagella; and Sporozoa (sporozoans), where the male gamete is flagellated and where movement by pseudopodia occurs only in immature stages.

During the life cycle of many protozoans some cells may produce a thick cell wall, lose water, and become dormant. During this stage, metabolism is reduced to a minimum or ceases entirely, and the dormant cell resists unfavorable environmental conditions such as drought, heat, increased salinity or unfavorable pH. Such a stage may be formed by mature, growing cells during asexual cycles of development or just after conjugation of gametes during sexual reproductive cycles. In protozoa, these cells are called "cysts." Cells going into the cyst stage are said to be "encysting."

After a physiologically and genetically determined period or, depending on species and type of cyst, when growth conditions again become favorable, the cell inside the cyst wall takes in water, resumes activity, bursts the cell wall, and emerges in the actively growing "trophozoite" stage. The encysted cell is said to have "excysted."

The term "ova" refers to the eggs of helminths and protozoa.

The term "larvae" means the wormlike form of a helminth or protozoa upon issuing from the ova.

Hence, the diagnosis of parasitic infection includes the detection of cysts, trophozoites, ova and larvae.

"Formaldehyde free" or "formalin free" refers to a composition which has undetectable levels of formaldehyde or formalin.

Examples of parasites that can be detected by the method of the invention include, but are not limited to *Entamoeba histolytica, Entamoeba hartimanii, Entamoeba coli,*

*Endolimax nana, Dientamoeba fragilis, Giardia lamblia, Chilomastix mesnili, Trichomonas vaginalis, Trichomonas hominis, blastocystis hominis,* Iodameoba sp., Enteromonas sps., Cryptosporium sps., *Isospora belli,* Acathamoeba sps., *Toxoplasma gondi, Enterobius vermicularis,* Trichuris sps., Strongyloides, *Schistosoma mansoni, Clonorchis sinensis, Necator americanus, Patagoniumus westermanii,* taenia sp., *Hymenolepis nana, Diphylobothrium latum, Schistosoma japonicum,* Toxocara sp., *Ascaris lumricoides, Schistosoma hematobium, Hymenolepis diminuta, Fasciola hepatica.*

The method of the invention uses a parasitological fixative which contains no formaldehyde, formalin, phenol, mercury or other harmful chemicals commonly associated with fixative compositions. Subsequent steps of the method utilize a slide fixative composition which improves the adhesion of sample material to the microscope slide. The use of the parasitological fixative composition and slide fixative composition in a single method provides significant advantages for processing fecal samples being analyzed for parasites.

According to the method of the invention, a fecal sample is added to a receptacle containing an effective amount of a parasitological fixative composition. In an important aspect of the invention, from about 1 to about 6 grams of fecal sample is added to a wide mouth, screw top centrifuge tube containing about 15 ml of fixative. The parasitological fixative is an aqueous solution containing from about 3 to about 5 weight percent glyceraldehyde.

The parasitological fixative also comprises from about 1 to about 2 weight percent of the salt of an organic acid having up to about 6 carbon atoms. The salt of an organic acid comprises organic acids selected from the group consisting of sodium acetate and potassium acetate. The organic acid buffers the composition at an acid pH which results in optimum conditions for subsequent visualization of parasites. In an important aspect of the invention the salt of the organic acid is sodium acetate.

The balance of the parasitological fixative comprises solvents. The parasitological fixative comprises from about 50 to about 55 volume percent of an alcohol selected from the group consisting of ethanol, methanol and butanol. The fixative also comprises from about 4.5 to about 5.0 volume percent of an alcohol selected from the group consisting of methanol, ethanol and butanol. In one aspect of the invention the parasitological fixative comprises from about 50 to about 55 weight percent ethanol and about 4.5 to about 5.0 volume percent methanol. The remainder of the parasitological fixative comprises from about 0.4 to about 0.5 volume percent methyl isobutyl ketone, and water.

In one aspect of the invention, the parasitological fixative is prepared by blending the above indicated components. Alternatively, the fixative is prepared by blending the indicated amounts of sodium acetate with NoToX™ histological fixative (Earth Safe Industries, Inc. Belle Mead, N.J.).

The parasitological fixative provides for the rapid killing of all elements in the sample and the preservation of the sample such that all components of the sample are maintained in a state which closely resembles the sample condition prior to fixing. The parasitological fixative composition provides fixation of the sample without the toxicity associated with typical fixatives. The parasitological fixative composition has an $LD_{50}>15$/kg, which is considered virtually non-toxic. The parasitological fixative composition can properly be disposed in a sewer system as the composition is biodegradable.

In addition to its lower toxicity, use of the parasitological fixative composition results in quicker and safer processing of samples with improved sample recovery. Processing of the fixed fecal sample requires the preparation of a concentrate. The sample is first filtered through wet gauze into a centrifuge tube. The total volume of the tube is brought to about 13 ml with saline and the sample is centrifuged. Saline is decanted, the pellet is resuspended with about 9 ml of saline, and sample is recentrifuged. The top layer of the centrifuged sample is rimmed with an applicator stick and the supernate is removed. Partitioning of the sample with an organic solvent such as ethyl ether or ethyl acetate is not required. Elimination of organic solvent partitioning steps improves the recovery of cysts up to about 78%, greatly increasing the accuracy of the diagnosis. Further, use of the method of the invention provides for clear nuclear definition of cysts. The concentrated sample is utilized for all subsequent analysis. Alternatively, organic solvent may be utilized for concentration of sample, but not for the preparation of samples for permanent staining.

About one drop of the concentrated sediment is removed to a microscope slide and inspected for parasites. The sediment sample can be mixed with a suitable stain, such as iodine, on the microscope slide to facilitate the identification of parasites in the sample. The use of the method of the invention provided for the optimum definition of parasites in the sample.

The remaining sediment is mixed with about one to two drops of slide fixative. The slide fixative comprises an effective amount of egg albumin, glycerin and an adhesion enhancing agent. Suitable egg albumins include those selected from the group consisting of avian egg albumin, bovine egg albumin, porcine egg albumin and equine egg albumin. Appropriate adhesion enhancing agents include silane derivatives selected from the group consisting of 3-aminopropyl-triethoxysilane. In an alternative aspect of the invention, the silane derivative can be replaced with an adhesion enhancing agent selected from the group consisting of poly-L-lysine, white glue, and Acry-Glide™ (Ameresco, Ohio).

About one drop of the sample/slide fixative mixture is applied to a slide and allowed to dry at room temperature. Slides can be further analyzed using commonly accepted staining techniques, such as the use of Trichrome stain, immunoassay, acid-fast stains, modified Trichrome stains, modified acid fast stains, hematoxylin stain, and fluorescent stains. Slides prepared according to the method of the invention provide clear and proper morphological characteristics with fine protozoal nuclear detail. Slide preparations dry rapidly and the method eliminates the alcohol-iodine step for staining.

In many typical staining procedures, slides are subjected to a series of steps where the slides are dipped into different concentrations of organic solvent (e.g. ethyl alcohol), allowed to drain, rinsed, stained, and then dipped into a clearing agent such as xylene. The manipulation of slides through the various dipping and rinsing steps can result in the loss of sample from the surface of the microscope slide. Loss of sample can result in inaccurate diagnosis and can lead to the preparation of more slides in an effort to insure against such loss. The slide fixative of the invention prevents sample loss during staining procedures and hence decreases the incidence of inaccurate diagnosis and extra sample preparation.

In another aspect of the invention, the slide fixative is utilized in combination with known histological methods to improve the adhesion of a wide variety of tissue and sample types to a glass microscope slide.

In an important aspect of the invention, the use of the parasitological fixative composition and the slide fixative composition of the method does not preclude the use of immunoassay techniques. Formaldehyde fixed samples are not acceptable for use with antibody staining techniques as formaldehyde can alter antibody binding sites such that antibody will not bind. Fluorescent antibody staining of samples prepared according to the method of the invention provided accurate and reliable results.

In another aspect, the invention provides a kit for the collection of fecal samples. The kit comprises a sealable transport bag containing one receptacle which contains the parasitological fixative composition of the invention and one clean receptacle. Both receptacles include a screw top with a sampling means effective for sampling fecal specimens extending down from and affixed to the screw top cap. In an important aspect of the invention, the sampling means is typically in the shape of a spoon, which facilitates sampling. A second clean receptacle is provided for the collection and transport of fecal specimens meant for culture. The sealable transport bag includes a protective pouch for specimen paperwork and provides for the safe, easy and convenient collection and transport of the fecal specimen.

The following examples illustrate methods for carrying out the invention and should be understood to be illustrative of, but not limiting upon, the scope of the invention which is defined in the appended claims.

EXAMPLES

EXAMPLE I

The recovery of cysts from fecal samples fixed in formalin and the glyceraldehyde based fixative composition of the invention was determined.

The same amount of Cryptosporidium oocysts was added to two fecal samples. One of the fecal samples was fixed in formalin the other in the glyceraldehyde based fixative composition of the invention. Samples were examined directly by making slide of each sample, and the number of cysts per 10 µl was determined.

Formaldehyde fixed samples were concentrated following commonly utilized procedures (Meridian Co. Cincinnati, Ohio). The formaldehyde sample was concentrated by first straining the sample through gauze into a centrifuge tube. The total volume of the tube was brought to 13 ml with saline. The sample was centrifuged and the supernate was decanted. The sediment was resuspended in saline, recentrifuged and saline was decanted. The sediment was resuspended in 10 ml of 10% formalin and vigorously mixed with 3 ml of ether. The mixture was centrifuged to form four layer, top layer, ether; second layer, plug of debris; third layer, formalin; and a bottom layer of sediment. After ringing the plug of debris from the sides of the tube with an applicator stick, the top three layers were decanted off. The number of cysts per 10 µl of concentrated sample was determined by direct examination, direct examination using acid-fast stain, and examination using direct fluorescent antibody.

The fecal sample fixed in the glyceraldehyde based fixative of the invention was concentrated according to the method of the invention. The fecal sample was first filtered through wet gauze into a centrifuge tube. The total volume of the tube was brought to 13 ml with saline and the sample was recentrifuged. Saline was decanted, the pellet was resuspended in 9 ml of saline, and the sample was centrifuged. The top layer of the centrifuged sample was rimmed with an applicator stick and the supernate was removed. The number of cysts per 10 µl of concentrated sample was determined by direct examination, direct examination using acid-fast stain, and examination using the direct fluorescent antibody technique.

The result of direct examination of samples for cysts before and after concentration were as follows:

|  | (cysts/10 µl) | |
| --- | --- | --- |
|  | Before Sample Concentration | After Sample Concentration |
| Sample fixed in Formaldehyde | 90 | 52 |
| Sample fixed in Glyceraldehyde | 102 | 234 |

The results of direct examination of samples for cysts using acid-fast staining were as follows:

|  | (cysts/10 µl) | |
| --- | --- | --- |
|  | Before Sample Concentration | After Sample Concentration |
| Sample fixed in Formaldehyde | 90 | 57 |
| Sample fixed in Glyceraldehyde | 105 | 182 |

The results of direct examination of samples for cysts using direct fluorescent antibody stain were as follows:

|  | (cysts/10 µl) | |
| --- | --- | --- |
|  | Before Sample Concentration | After Sample Concentration |
| Sample fixed in Formaldehyde | 45 | 80 |
| Sample fixed in Glyceraldehyde | 110 | 205 |

EXAMPLE II

The recovery of Giardia cysts from concentrated and unconcentrated fecal samples was determined following the procedures indicated in Example I. Cysts were counted using iodine and direct antibody stains. In addition the number of cysts recovered from samples preserved in polyvinyl alcohol was determined.

The result of direct examination of samples for cysts using direct fluorescent antibody was as follows:

|  | (cysts/10 µl) | |
| --- | --- | --- |
|  | Before Sample Concentration | After Sample Concentration |
| Sample fixed in Formaldehyde | 60 | 32 |
| Sample fixed in Glyceraldehyde | 95 | 150 |

The results of direct examination of samples for cysts using Trichrome stained slides were as follows:

|  | (cysts/10 μl) |
|---|---|
| Sample fixed in polyvinyl alcohol | 48 |
| Sample fixed in Glyceraldehyde | 216 |

The results of direct examination of samples for cysts using iodine stain were as follows:

|  | (total cysts) |
|---|---|
| Sample fixed in Formaldehyde | 1700 |
| Sample fixed in Glyceraldehyde | 4000 |

Particular features of the invention are emphasized in the claims which follow.

What is claimed is:

1. A method for preserving fecal specimens, said method comprising contacting a fecal specimen with an amount of a parasitological preservative effective for preserving a fecal specimen, said preservative comprising from about 3 to about 5 weight percent glyceraldehyde; from about 1 to about 2 weight percent of a salt of an organic acid, said organic acid comprising up to about 6 carbon atoms; organic solvent and water.

2. The method of claim 1 wherein the salt of the organic acid is selected from the group consisting of sodium acetate and potassium acetate.

3. The method of claim 2 wherein the salt of the organic acid is sodium acetate.

4. The method of claim 1 wherein the organic solvent comprises from about 50 to about 55 volume percent of an alcohol selected from the group consisting of ethanol, methanol and butanol, from about 4.5 to about 5.0 volume percent of an alcohol selected from the group consisting of methanol, ethanol and butanol, and from about 0.4 to about 0.5 volume percent methyl isobutyl ketone.

5. The method of claim 4 wherein the organic solvent comprises from about 50 to about 55 volume percent ethanol, from about 4.5 to about 5.0 volume percent methanol, and from about 0.4 to about 0.5 volume percent methyl isobutyl ketone.

6. A method for preserving, concentrating and staining focal specimens being analyzed for ova or parasites, said method comprising:

a) contacting a fecal specimen with a preservative, said parasitological preservative comprising from about 3 to about 5 weight percent glyceraldehyde, from about 1 to about 2 weight percent of a salt of an organic acid, said organic acid comprising up to about 6 carbon atoms, organic solvent and water;

b) sedimenting the fecal specimen of step a) through a method comprising filtration and centrifugation;

c) applying about one drop of the sedimented fecal sample to a microscope slide whereby ova in the fecal specimen are rendered detectable;

d) contacting a slide fixative with the sedimented fecal specimen of step b), said slide fixative comprising from about 40 to about 60 weight percent of a protein solution, from about 40 to about 60 weight percent glycerin and from about 0.1 to about 0.9 weight percent of an adhesion enhancing agent; and e) applying about one drop of the specimen from step d) to a microscope slide and staining said specimen for identification of parasites.

7. The method of claim 6 wherein the protein solution comprises a protein selected from the group consisting of avian egg albumin, bovine egg albumin, porcine egg albumin and equine egg albumin.

8. The method of claim 6 wherein the adhesion enhancing agent is 3-aminopropyl-triethoxysilane.

9. The method of claim 6 wherein the adhesion enhancing agent is poly-L-lysine.

10. The method of claim 6 wherein the salt of the organic acid is selected from the group consisting of sodium acetate and potassium acetate.

11. The method of claim 10 wherein the organic acid is sodium acetate.

12. The method of claim 6 wherein the organic solvent comprises from about 50 to about 55 volume percent of an alcohol selected from the group consisting of ethanol, methanol and butanol, from about 4.5 to about 5.0 volume percent of an alcohol selected from the group consisting of methanol, ethanol and butanol, and from about 0.4 to about 0.5 volume percent methyl isobutyl ketone.

13. The method of claim 12 wherein the organic solvent comprises from about 50 to about 55 volume percent ethanol, from about 4.5 to about 5.0 volume percent methanol, and from about 0.4 to about 0.5 volume percent methyl isobutyl ketone.

14. A method for preserving fecal specimens, said method comprising contacting a fecal specimen with an amount of a parasitological preservative effective for preserving a fecal specimen, said preservative comprising from about 3 to about 5 weight percent glyceraldehyde; from about 1 to about 2 weight percent of a salt of an organic acid, said organic acid comprising up to about 6 carbon atoms; organic solvent and water, wherein the organic solvent is selected from the group consisting of methanol, ethanol, butanol and methyl isobutyl ketone.

15. The method of claim 14 wherein the salt of the organic acid is selected from the group consisting of sodium acetate and potassium acetate.

16. The method of claim 15 wherein the organic solvent comprises from about 50 to about 55 volume percent of an alcohol selected from the group consisting of ethanol, methanol and butanol, from about 4.5 to about 5.0 volume percent of an alcohol selected from the group consisting of methanol, ethanol and butanol, and from about 0.4 to about 0.5 volume percent methyl isobutyl ketone.

\* \* \* \* \*